(12) United States Patent
Ducharme et al.

(10) Patent No.: US 8,419,677 B2
(45) Date of Patent: Apr. 16, 2013

(54) BALLOON-TIPPED ENDOSCOPIC SYSTEM

(75) Inventors: Richard W. Ducharme, Winston-Salem, NC (US); Tyler Evans McLawhorn, Winston-Salem, NC (US)

(73) Assignee: Cook Medical Technologies, LLC, Bloomington, IN (US)

( * ) Notice: Subject to any disclaimer, the term of this patent is extended or adjusted under 35 U.S.C. 154(b) by 396 days.

(21) Appl. No.: 12/641,872

(22) Filed: Dec. 18, 2009

(65) Prior Publication Data

US 2010/0168612 A1 Jul. 1, 2010

Related U.S. Application Data

(60) Provisional application No. 61/141,568, filed on Dec. 30, 2008.

(51) Int. Cl.
*A61M 29/00* (2006.01)
*A61F 2/06* (2006.01)

(52) U.S. Cl.
USPC ...................... 604/96.01; 623/1.11

(58) Field of Classification Search .. 604/96.01–103.14; 623/1.1, 1.11
See application file for complete search history.

(56) References Cited

U.S. PATENT DOCUMENTS

| | | | |
|---|---|---|---|
| 4,931,037 A * | 6/1990 | Wetterman | 604/8 |
| 5,178,608 A * | 1/1993 | Winters | 604/102.02 |
| 5,395,389 A * | 3/1995 | Patel | 606/194 |
| 6,059,809 A | 5/2000 | Amor et al. | |
| 6,117,104 A * | 9/2000 | Fitz | 604/96.01 |
| 6,253,443 B1 * | 7/2001 | Johnson | 29/557 |
| 6,270,489 B1 * | 8/2001 | Wise et al. | 604/508 |
| 6,364,867 B2 * | 4/2002 | Wise et al. | 604/509 |
| 6,443,979 B1 * | 9/2002 | Stalker et al. | 623/1.11 |
| 6,537,247 B2 * | 3/2003 | Shannon | 604/103.05 |
| 7,192,440 B2 * | 3/2007 | Andreas et al. | 623/1.11 |
| 2001/0016726 A1 * | 8/2001 | Dubrul et al. | 604/509 |
| 2003/0208222 A1 | 11/2003 | Zadno-Azizi | |
| 2005/0131446 A1 | 6/2005 | Coughlin et al. | |
| 2007/0060942 A2 | 3/2007 | Zadno-Azizi | |

FOREIGN PATENT DOCUMENTS

| WO | WO 03/077983 A1 | 9/2003 |
|---|---|---|
| WO | WO 2006/073870 A2 | 7/2006 |

* cited by examiner

*Primary Examiner* — Max Hindenburg
*Assistant Examiner* — John Pani
(74) *Attorney, Agent, or Firm* — Brinks Hofer Gilson & Lione

(57) ABSTRACT

Multi-luminal endoscopic systems for sterilely delivering deployable devices or obtaining bodily tissues. The system comprise an outer catheter comprising a wall that encloses an outer lumen; an inner catheter movably disposed within the outer lumen and having an inner lumen; a balloon-tipped catheter movably disposed within the inner lumen and having a distal end and a proximal end, wherein the distal end of the balloon-tipped catheter comprises a balloon tip that can be expanded to contact the wall of the outer catheter to provide a seal to prevent bodily fluids from entering the outer lumen; and a push catheter having a lumen and is located within the outer lumen. The delivery systems can comprise concentric catheters. Systems used for tissue collecting can comprise catheters with different common center.

15 Claims, 6 Drawing Sheets

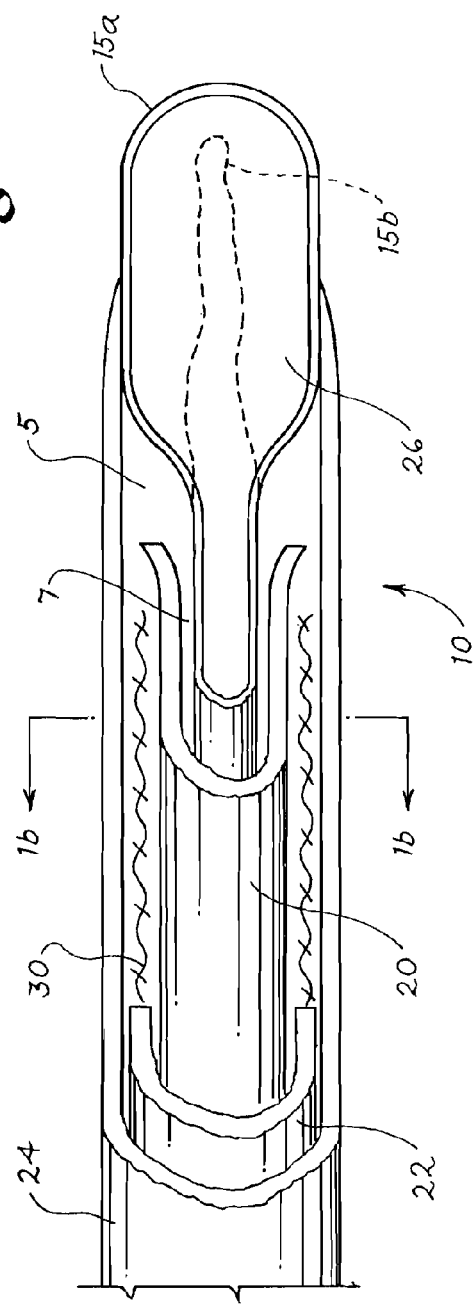

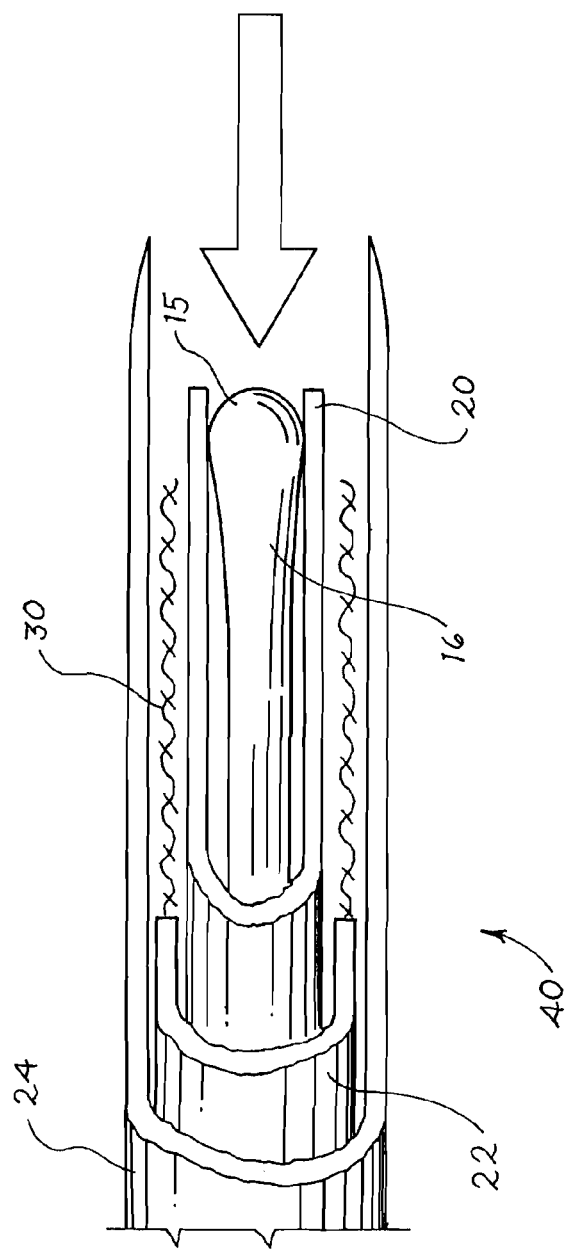

BALLOON-TIPPED ENDOSCOPIC SYSTEM

CROSS-REFERENCE TO RELATED APPLICATIONS

This application claims priority to U.S. Provisional Application No. 61/141,568, filed on Dec. 30, 2008, the entire contents of which are hereby incorporated by reference.

TECHNICAL FIELD

The present invention relates to ballooned-tipped endoscopic devices useful in natural orifice transluminal endoscopy surgery. The systems can be used to deploy therapeutic devices and obtain tissue samples.

BACKGROUND

Openings or perforations in the walls of internal organs and vessels may be naturally occurring, or formed intentionally or unintentionally. These openings may be used to gain access to adjacent structures of the body, such techniques being commonly referred to as transluminal procedures. For example, culdoscopy was developed over 70 years ago, and involves transvaginally accessing the peritoneal cavity by forming an opening in the cul de sac. This access to the peritoneal cavity allows medical professionals to visually inspect numerous anatomical structures, as well as perform various procedures such as biopsies or other operations, such as tubal ligation. Many transluminal procedures for gaining access to various body cavities using other bodily lumens have also been developed. One field of procedures has been referred to as Natural Orifice Transluminal Endoscopy Surgery ("NOTES"). Natural orifices such as the mouth, nose, ear, anus, or vagina may provide access to such bodily lumens and cavities. The bodily lumen(s) of the gastrointestinal tract are often endoscopically explored and can be utilized to provide access to the peritoneal cavity and other body cavities, all in a minimally invasive manner. U.S. Patent Application No. 60/872,023 filed Feb. 28, 2007, discloses such a procedure, and is incorporated herein by reference in its entirety.

Compared to traditional open surgery or laparoscopic surgery, transluminal procedures are less invasive by eliminating abdominal incisions (or other exterior incisions) and incision related complications, while also reducing postoperative recovery time, reducing pain, and improving cosmetic appearance. At the same time, there remain challenges to transluminal procedures, including providing a suitable conduit to the openings and body cavities, robust medical devices that are maneuverable via the conduit and operable within the body cavity, sterility of the conduit, maintaining insufflation of the body cavity, proper closure of the opening and prevention of infection. For example, when an opening is formed in a bodily wall of the gastrointestinal tract, such as in the stomach or intestines, spillage of the stomach contents, intestinal contents or other bodily fluids into the adjacent body cavity can occur. Travel of bacteria laden fluids outside of the gastrointestinal tract may cause unwanted and sometimes deadly infection.

One of the current challenges in NOTES procedures is sterile delivery of a material into the peritoneum and obtaining tissue samples in a sterile way.

BRIEF SUMMARY

Herein provided is a multi-luminal system comprising an outer catheter comprising a wall that encloses an outer lumen; an inner catheter movable disposed within the outer lumen and having an inner lumen; a balloon-tipped catheter movably disposed within the inner lumen and having a distal end and a proximal end, wherein the distal end of the balloon-tipped catheter comprises a balloon tip that can be expanded to contact the wall of the outer catheter to provide a seal to prevent bodily fluids from entering the outer lumen; and a deployable device within the outer lumen.

The system can also comprise a push catheter that has a lumen and is located within the outer lumen with a first position proximal to the distal end of the balloon-tipped catheter. The outer lumen can further comprise a deployable device with the push catheter proximally abutting the deployable device. The inner catheter can comprise a push mechanism that proximally abuts the deployable device. The system can comprise concentric outer, inner, push, and balloon-tipped catheters. The system can comprise concentric inner and balloon-tipped catheters. The inner and push catheters may not be concentric in some systems.

Also described herein is a method of delivery using a multi-luminal delivery system, the system comprising an outer catheter comprising a wall that encloses an outer lumen; an inner catheter movably disposed within the outer lumen and having an inner lumen; a balloon-tipped catheter movably disposed within the inner lumen having a proximal end and distal end comprising a balloon tip that can be expanded to contact the wall of the outer catheter to provide a seal to prevent bodily fluids from entering the outer lumen; and a deployable device about the inner catheter. The method comprises introducing the system into an endoluminal vessel until the balloon tip reaches a desired location; deflating the balloon tip; placing the deflated balloon tip within the inner lumen of the catheter; and deploying the deployable device by manipulating the outer catheter relative to the inner catheter such that the deployable device is distal to the outer catheter.

Herein described also is a multi-luminal tissue collecting system. The system comprises an outer catheter comprising a wall that encloses an outer lumen; a first inner catheter movably disposed within the outer lumen and having an inner lumen; a balloon-tipped catheter movably disposed within the inner lumen and having a distal end comprising a balloon tip and a proximal end, wherein the balloon tip can be expanded to contact the wall of the outer catheter to provide a seal to prevent bodily fluids from entering the outer lumen; a second inner catheter having a lumen and located within the outer lumen, the lumen of the second inner catheter comprising a tissue collecting mechanism; and wherein the first inner catheter and the second catheter are not concentric. The method of using the tissue collecting system comprises introducing the system into an endoluminal vessel until the balloon tip reaches a desired location; deflating the balloon tip; retracting the deflated distal end of the balloon tip catheter through the inner catheter; and deploying the biopsy needle through the push catheter; retracting the biopsy needle into the push catheter; and inflating the distal end of the balloon tip.

BRIEF DESCRIPTION OF THE DRAWINGS

FIG. 1a is a cutaway perspective view of the delivery system with the inflated balloon having solid lines and the deflated balloon having dashed lines.

FIG. 1b is a cross-sectional view of the delivery system.

FIG. 1c is a cross-sectional view of an alternative delivery system.

FIG. 2 is a cutaway perspective view of the delivery system with the balloon tip deflated and into the inner catheter.

DETAILED DESCRIPTION OF THE DRAWINGS AND THE PRESENTLY PREFERRED EMBODIMENTS

Figure 3:
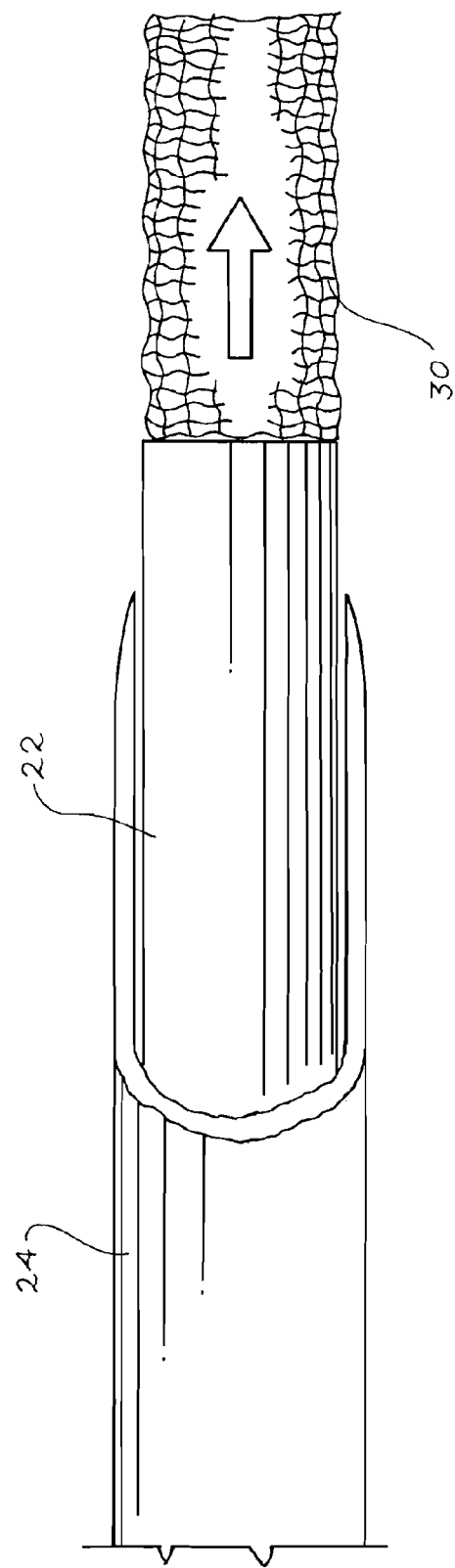
FIG. 3 is a cutaway perspective view of the push catheter advancing the hernia mesh.

The term "prosthesis" means any replacement for a body part or for a function of that body part or any device that enhances or adds functionality to a physiological system.

The term "stent" means any device that provides rigidity, expansion force, or support to a prosthesis, such as a stent graft. In one configuration, the stent may represent a plurality of discontinuous devices. In another configuration, the stent may represent one device. Stents may have a wide variety of configurations and may be balloon-expandable or self-expanding. Typically, stents have a circular cross-section when fully expanded, so as to conform to the generally circular cross-section of a body lumen. In one example, a stent may comprise struts (elongate portions) and acute bends (curvilinear portions) that are arranged in a zigzag configuration in which the struts are set at angles to each other and are connected by the acute bends. Although an undulating configuration is used throughout this application, it is understood that the stent may have a sinusoidal or a zigzag configuration as well. One example of a stent configuration is a Z-stent. The stents as described in this disclosure may be attached to the exterior of the graft, the interior of the graft, and/or may be sandwiched between two or more layers of graft material.

A variety of biocompatible materials may be employed to construct the stent, or portions of the stent, including metals and/or alloys, medically acceptable polymers, and/or bioabsorbable polymers or materials. The metals and/or alloys may, among other things, include stainless steel, tantalum, nitinol, gold, silver, tungsten, platinum, inconel, cobalt-chromium alloys, and iridium, all of which are commercially available metals or alloys used in the fabrication of medical devices. In a preferred configuration, the stent is constructed from nitinol, stainless steel, and/or cobalt-chromium alloys.

The term "graft or graft material" means a generally cannular or tubular member which acts as an artificial vessel or prosthesis. A graft by itself or with the addition of other elements, such as structural components, can be an endoluminal prosthesis. The graft comprises a single material, a blend of materials, a weave, a laminate, or a composite of two or more materials.

The term "catheter" generally means medical devices including balloon-tipped catheters, guide catheters, and delivery catheters.

The term "deployable device" generally means a medical device that provides therapeutic treatment to a medically treatable area of an animal body. Deployable devices include, but are not limited to, a hernia mesh, ligating barrel, jejunal magnet, or stent graft.

FIG. 1a shows a multi-luminal delivery system 10 that minimizes the introduction of bacteria into the peritoneum and the risk of contaminating a sterile deployable device. The system is comprised of catheters that are roughly concentric and contain a deployable device that may be too large for placement in the access channel of an endoscope. The system can be introduced into the gastrointestinal tract through the mouth or other natural bodily orifice.

As shown in FIG. 1a, the system 10 comprises: an outer catheter 24, an inner catheter 20, a push catheter 22, and a balloon-tipped catheter 26. The outer catheter 24 comprises a wall that encloses an outer lumen 5. The inner catheter 20 is within the outer lumen 5 and has an inner lumen 7 that contains, at least partially, the balloon-tipped catheter 26. The distal end of the inner catheter 20 flares outwardly to prevent the accumulation of potentially harmful bacteria from collecting on the outside of the inner catheter 20 and from contacting the sterile deployable device 30. The distal end of the balloon-tipped catheter 26 has a balloon tip 15 that contacts the wall of the outer catheter 24 and provides a seal to prevent bacteria or other potentially harmful fluids from entering the outer lumen 5.

The ballooned-tipped catheter 26 has a proximal elongated catheter shaft 16 that is within the inner lumen 7 of the inner catheter 20 while on the distal end there is a balloon tip 15. It is understood that the distal end of the balloon-tipped catheter 26, the actual balloon tip 15, has a first diameter when inflated and a second diameter when deflated. The deflated balloon tip 15b having the second predetermined diameter is shown in dashed lines. The inflated balloon tip 15a, which has solid lines, contacts the inner wall of the distal end of the outer catheter 24 wall such that blood and other bodily fluids are prevented from entering the outer lumen and the contents of the outer catheters as well as the deployable device 30. It is understood that balloon-tipped catheters are manufactured in a variety of arrangements. The present invention comprises balloon-tipped catheters that provide an expandable portion, whether on the distal tip or along the shaft, that contacts the outer catheter to provide a seal. The balloon-tipped catheter, once expanded can contact the inner wall, outer wall, or the distal edge of the catheter to provide a seal.

Figure 4:
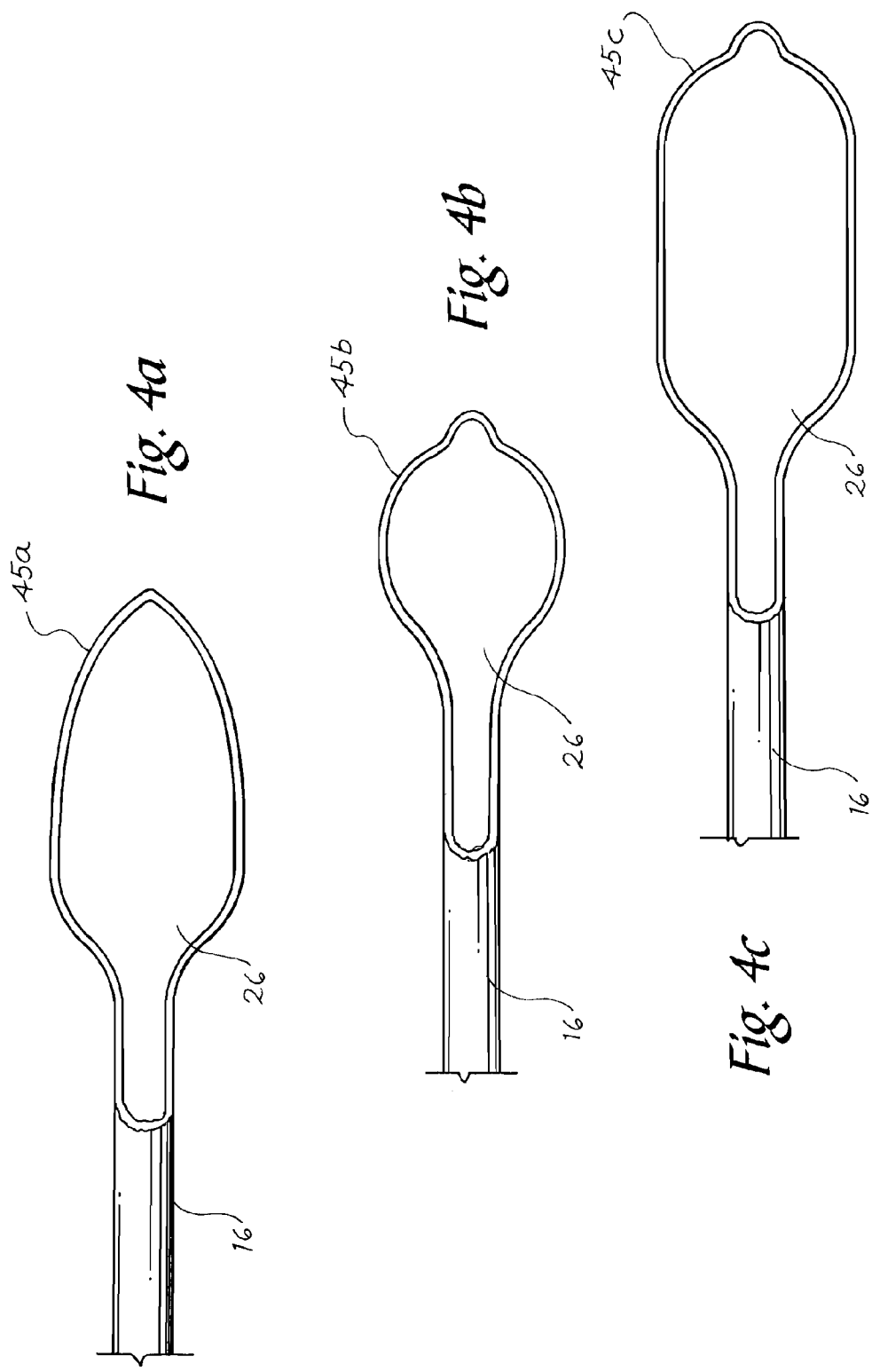
FIGS. 4a, 4b, and 4c are perspective views of different types of balloon tips.

The balloon-tipped catheter 26 can be made of materials capable of elastic expansion typically used in the field. For example, the balloon-tipped catheter 26 can comprise silicone, latex, or any other suitable material commonly used in the field. As shown in FIGS. 4a, 4b, and 4c, the balloon tip 15 can be tapered 45a, bulbous 45b, or cylindrical 45c. The balloon-tipped catheter 26 can comprise a wire guide to assist in guiding the entire system 10 throughout the gastrointestinal tract. The balloon tip 15 can have a nipple like tip to assist in advancing the catheter. When using a non-self-expanding deployable device, the balloon tip 15 may be preferable over a standard end cap because less lateral space is used during deployment.

The push catheter 22 is within the outer lumen and generally has the same diameter as the deployable device 30. The deployable device shown in FIG. 2 is a hernia mesh 30. The push catheter 22 is shown in a first position in FIG. 2. This first position 40 is proximal to the balloon tip 15. The first position 40 is generally the push catheter's 22 initial position when the system 10 is inserted into the human body. The push catheter 22 is in the first position 40 when the deployable device 30 is not yet delivered or advanced out of the outer catheter 24 and the balloon tip 15 is still expanded and in contact with the wall of the outer catheter 24. FIG. 2 shows the balloon tip 15 deflated and withdrawn into the inner catheter 20. The push catheter's 22 second position 45 is obtained when it is advanced to deliver the deployable device 30, as shown in FIG. 3. Here, the second position 45 is distal to the balloon tip 15 and the outer catheter 24 such that the hernia mesh 30 is completely clear of the outer catheter 30. As shown in FIG. 2, the distal end of the inner catheter 20 can be parallel with the remainder of the catheter so as to not obstruct the delivery of the delivery device 30 if it is pushed by the push catheter 22 in a distal direction. There are systems, such as in FIG. 1a, with the flared end on the inner catheter 20 where the deployable device 30 is delivered by retracting the outer catheter 24.

Figures 5, 5A:
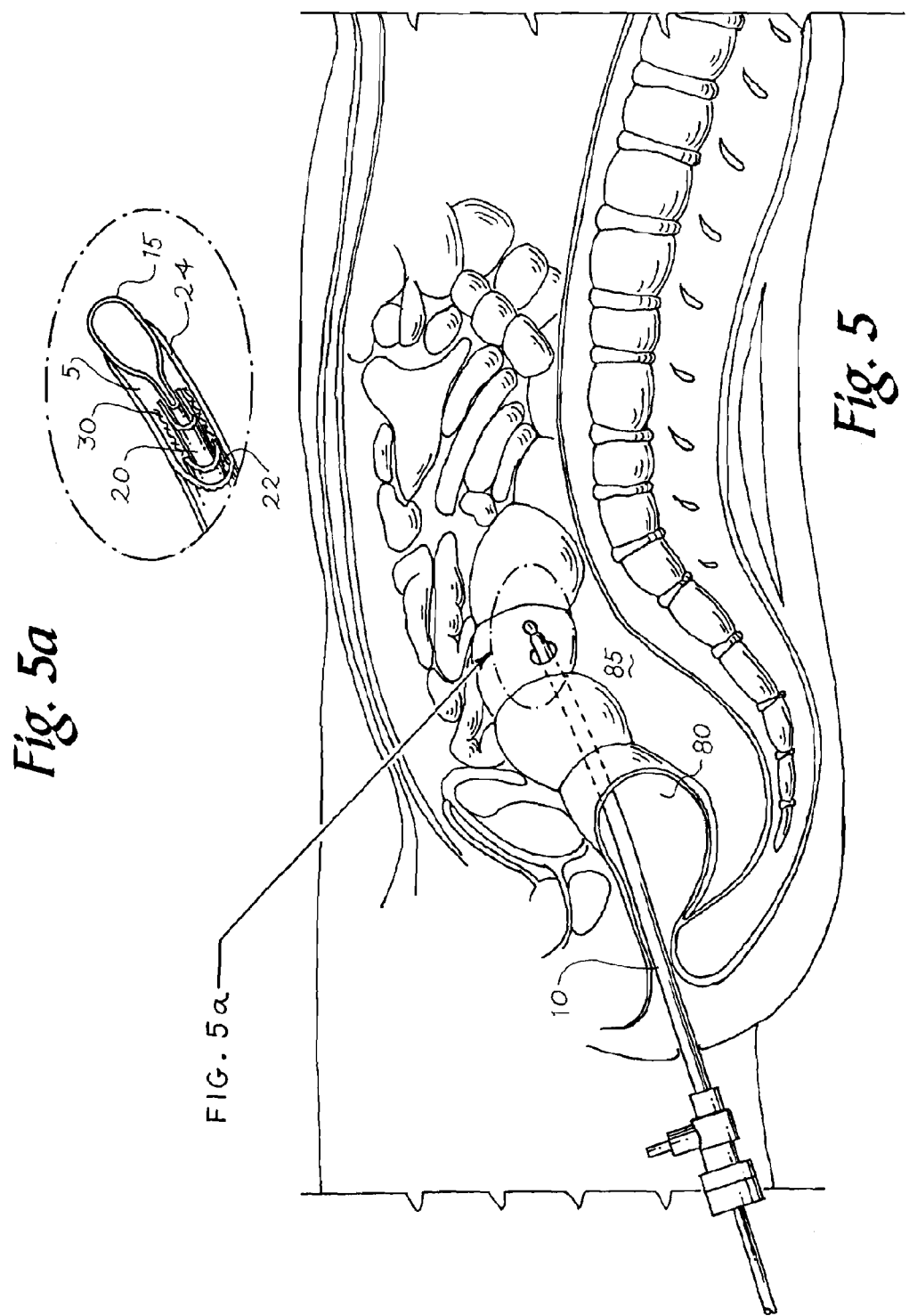
FIG. 5 is a cutaway view of a human abdomen with the delivery system being inserted into a human anus.
FIG. 5a is a zoom view of the distal end of the system.

The inner lumen 7 of the inner catheter 20 comprises the proximal elongated shaft 16 of the ballooned-tipped catheter 26. When the balloon tip 15 is deflated, it is retracted into the inner lumen 7. While within the inner catheter 20, the balloon tip 15 and any other bodily fluids on it are separated from the deployable device 30. The deployable device 30 is kept separate from the balloon tip 15 to maintain the device's sterility until implantation. The seal provided by the balloon tip 15 minimizes the possibility of transferring bacteria or other microorganisms that may be considered harmful from a first environment into a second environment. As seen in FIG. 5, the system 10 travels through the colon 80 and out of an incision into the peritoneum 85. The system 10 may be exposed to fluids and bacteria in both environments. The seal helps prevent material found in the colon 80 from entering the outer lumen 5 and being transferred to a second environment, such as the peritoneum 85. Once the balloon tip 15 is withdrawn inside the inner catheter 20, the push catheter 22 can be advanced distally to deploy the deployable device, the hernia mesh 30, out of the outer catheter 24.

FIG. 1b is a cross sectional view of the system showing the concentric placement of the catheters. The push catheter 22 cannot be seen in this figure as its diameter is similar to the diameter of the deployable device 30. The deployable device 30 and the push catheter 22 have smaller diameters than the outer catheter 24 but larger diameters than the inner catheter 20. Although a hernia mesh 30 is shown in these figures as the deployable device, other devices can be delivered using this system. The system can also be used to deliver, for example, gauzes of any type, large volumes of fluid or powders, specimen retrieval bags, or slings. The deployable device can be a stent graft, ligating bands, or jejunal magnets. The deployable device can be any device used in endoscopy but is too large to fit in the accessory channel of an endoscope. The deployable devices may require other accoutrements for delivery. For instance, if actuating wires are needed for delivery of a stent graft they can be carried within the push catheter 22. Similarly, activation lines may be carried within the push catheter 22 for delivering ligating bands.

The system 10 can also comprise a wire guide to assist in delivery. The system can also be adapted to accommodate joystick manipulation.

Figure 6:
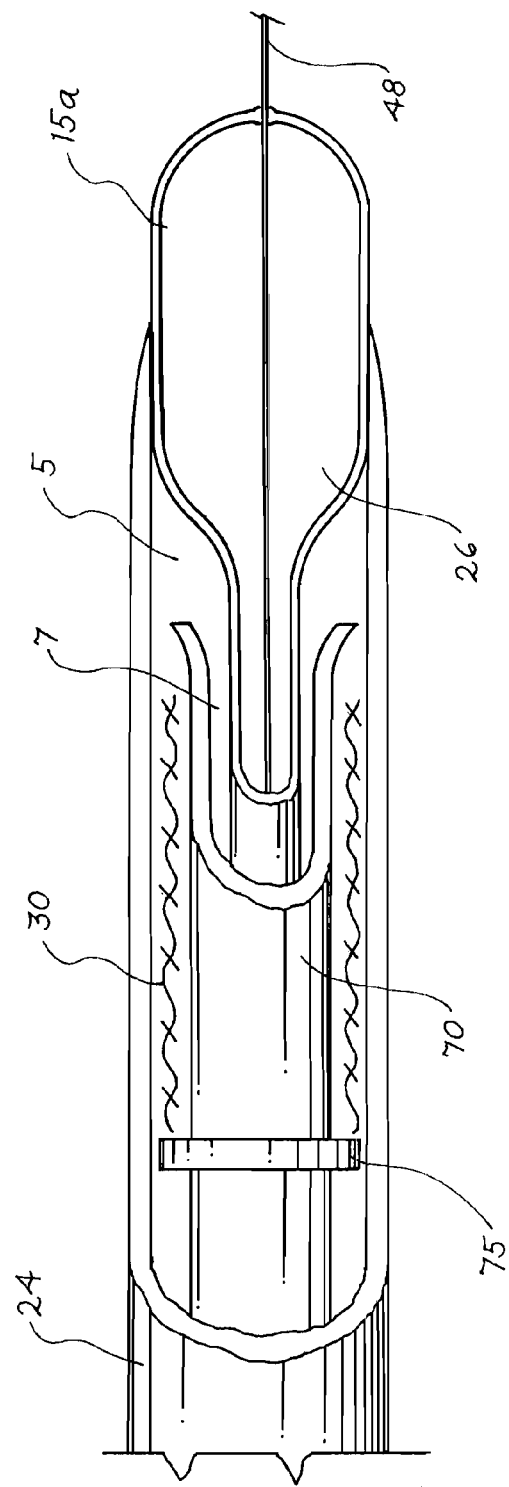
FIG. 6 is a cutaway perspective view of the delivery system with an inner catheter used to deliver a deployable device.

In FIG. 6, a system 10 is shown that comprises an inner catheter 70 that is capable of deploying the deployable device 30. This inner catheter 70 may comprise a push mechanism to assist in deploying the deployable device 30. The push mechanism can be a ridge 75 having a diameter slightly larger than the diameter of the inner catheter 70 that proximally abuts the proximal end of a deployable device 30. The ridge 75 may be used to advance the deployable device 30 out of the outer lumen 5 or hold the deployable device 30 in place while the outer catheter 24 is retracted. The ridge 75 can be radiopaque. The balloon tip 15 also comprises a wire guide 48 to assist in placing the system 10.

The system is used to deliver deployable devices through a natural bodily orifice, such as the mouth, nose, or anus, with the balloon inflated to seal off bodily fluids. Through the mouth, the system would be able to access the upper gastrointestinal tract, the stomach, the duodenum, and the small intestine. Through the anus, the system could access the colon, which includes the large and small intestine. A system having comparable diameter can access the sinuses through the nose. Other areas of the body can be accessed with internal incisions in the stomach, vagina, bladder, or colon to perform procedures such as appendectomies, gastric revisions, ligation, or biopsies.

In FIG. 5, the system 10 is introduced into a human anus and advanced through the rectum and into the colon until the balloon tip 15 reaches a desired location. The system can be introduced transrectally, transvaginally, or transgastrically. The balloon tip 15 provides a seal to prevent bodily fluids from entering the outer lumen and contaminating the sterile deployable device. Because of its flexibility and contour, the balloon-tipped catheter 26 acts as a flexible tip to the system 10 that prevents damage to the anatomy as the system 10 winds its way through the gastrointestinal tract to the desired location.

The multi-luminal system can comprise catheters that can be used for tissue collecting which have different common centers. FIG. 1b shows a cross-sectional view of a system where the outer catheter 24, the inner catheter 20, the balloon-tipped catheter 26, and the push catheter 22 all have a common center. FIG. 1c shows a cross-sectional view of system where a first inner catheter 60 and the balloon-tipped catheter 26 share a common center different than the common center shared by the second inner catheter 62. The system can be used in biopsy procedures to obtain tissue specimens. The system is delivered with the balloon tip 15 expanded to keep a biopsy needle 48 or any other tissue collecting mechanism within the second inner catheter 62 from being contaminated by bodily fluids. Once the balloon tip 15 reaches the desired location, the balloon tip 15 is deflated and the biopsy needle 48 is advanced to obtain the tissue sample. Once the tissue specimen is obtained, the balloon tip 15 can be re-expanded to shield the contents of the outer lumen 5 and to prevent the tissue from being contaminated during the retrieval process. This configuration can also contain retrieval bags to obtain bodily specimens and to prevent them from being contaminating or contaminating other parts of the anatomy while retrieving the system.

In FIG. 1c, the balloon-tipped catheter 26 and the first inner catheter 60 are still concentric. When expanded in this configuration, the balloon tip 15 engages the wall of the outer catheter 24 to seal off the contents of the outer lumen 5, which includes the first inner catheter 60, the second inner catheter 62, and the biopsy needle 48 in FIG. 1c. In this configuration, the push catheter 22 has a lumen that comprises at least one biopsy needle 48. The lumen of the second inner catheter 62 can also comprise a retrieval bag.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A multi-luminal delivery system comprising:
an outer catheter comprising a distal end and a wall that encloses an outer lumen;

an inner catheter movably disposed within the outer lumen and having an inner lumen, the inner catheter having a distal end disposed proximally of the distal end of the outer catheter;

a balloon-tipped catheter movably disposed within the inner lumen of the inner catheter and having a distal end and a proximal end, wherein the distal end of the balloon-tipped catheter comprises an expandable balloon tip that is disposed distally of the distal end of the inner catheter, the balloon tip being expanded into contact with the wall of the outer catheter near the distal end of the outer catheter so as to provide a seal to prevent bodily fluids from entering the outer lumen of the outer catheter; and a deployable device disposed within the outer lumen proximally of the expanded balloon tip.

2. The delivery system of claim 1 further comprising a push catheter having a lumen and located within the outer lumen with a first position proximal to the distal end of the balloon-tipped catheter.

3. The delivery system of claim 2 where the inner and outer catheters are concentric, and the inner lumen of the inner catheter is located within the lumen of the push catheter.

4. The delivery system of claim 2 where the inner catheter and push catheter are not concentric.

5. The delivery system of claim 1 where the deployable device is a medical device that is configured to provide a therapeutic treatment to an animal body.

6. The delivery system of claim 1 wherein the deployable device is disposed about the inner catheter and proximal of the distal end of the inner catheter, and the inner catheter further comprises a push mechanism for deploying the deployable device.

7. The delivery system of claim 1 where the proximal end of the balloon-tipped catheter is an elongated catheter shaft movably disposed within the inner lumen of the inner catheter and the balloon tip has a first predetermined diameter when inflated and a second predetermined diameter when deflated.

8. The delivery system of claim 1 further comprising a second inner catheter having a common center and wherein the inner catheter and the balloon-tipped catheter have a common center different than the second inner catheter.

9. A method of delivering a deployable device using a multi-luminal delivery system, the system comprising:

an outer catheter comprising a wall that encloses an outer lumen;

an inner catheter movably disposed within the outer lumen and having an inner lumen;

a balloon-tipped catheter movably disposed within the inner lumen of the inner catheter and having a proximal end and a distal end, the distal end comprising a balloon tip disposed distally of the inner catheter, wherein the balloon tip is expanded to contact the wall of the outer catheter to provide a seal to prevent bodily fluids from entering the outer lumen of the outer catheter; and the deployable device located about the inner catheter;

said method comprising:

expanding the balloon tip into contact with wall of the outer catheter so as to seal the outer lumen of the outer catheter;

introducing the system into an endoluminal vessel until the balloon tip reaches a desired location;

deflating the balloon tip;

retracting the deflated balloon tip within the inner lumen of the inner catheter; and deploying the deployable device by manipulating the outer catheter relative to the inner catheter such that the deployable device is distal to the outer catheter.

10. The method of claim 9 further comprising a push catheter having a lumen, the push catheter being movably disposed within the outer lumen, the push catheter being configured for delivering the deployable device.

11. The method of claim 9 where the endoluminal vessel is the gastrointestinal tract.

12. The method of claim 9 where the deployable device is a medical device that provides a therapeutic treatment to an animal body.

13. The method of claim 9 where the system is introduced through the mouth of an animal.

14. The method of claim 9 where the desired location is within the gastrointestinal tract.

15. The method of claim 9 further comprising monitoring the introduction and the deployment using fluoroscopy.

* * * * *